(12) United States Patent
Roitman

(10) Patent No.: US 7,312,040 B2
(45) Date of Patent: Dec. 25, 2007

(54) MICROCAPSULE BIOSENSORS AND METHODS OF USING THE SAME

(75) Inventor: Daniel B. Roitman, Menlo Park, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 684 days.

(21) Appl. No.: 10/247,840

(22) Filed: Sep. 20, 2002

(65) Prior Publication Data

US 2004/0058381 A1    Mar. 25, 2004

(51) Int. Cl.
*G01N 33/53*    (2006.01)

(52) U.S. Cl. ..................................... 435/7.1

(58) Field of Classification Search ............... 435/7.1, 435/4, 7.8, 7.93, 7.94, 7.95, 283.1, 287.1, 435/287.2, 287.7, 287.9, 288.3, 288.7, 810, 435/973, 6, 7.92; 436/514, 518, 523–535, 436/546–548, 169, 172; 422/50, 52, 55, 422/56, 57, 58, 61, 68.1, 69, 73, 82.05, 82.07, 422/82.08, 82.09

See application file for complete search history.

(56) References Cited

U.S. PATENT DOCUMENTS

| | | | | |
|---|---|---|---|---|
| 4,156,764 A | * | 5/1979 | White | .......... 526/211 |
| 4,399,209 A | | 8/1983 | Sanders et al. | |
| 4,562,137 A | | 12/1985 | Sanders | |
| 4,743,560 A | * | 5/1988 | Campbell et al. | .......... 436/501 |
| 5,059,261 A | | 10/1991 | Condo et al. | |
| 5,128,241 A | | 7/1992 | Imai et al. | |
| 5,221,613 A | | 6/1993 | Kida et al. | |
| 5,393,527 A | | 2/1995 | Malick et al. | |
| 5,518,883 A | | 5/1996 | Soini | |
| 5,593,843 A | | 1/1997 | Malick et al. | |
| 5,620,903 A | | 4/1997 | Malick et al. | |
| 5,688,697 A | | 11/1997 | Malick et al. | |
| 5,736,330 A | | 4/1998 | Fulton | |
| 5,786,219 A | | 7/1998 | Zhang et al. | |
| 5,916,727 A | | 6/1999 | Camillus et al. | |
| 5,981,719 A | | 11/1999 | Woiszwillo et al. | |
| 6,057,107 A | | 5/2000 | Fulton | |
| 6,127,084 A | | 10/2000 | Katampe et al. | |
| 6,361,944 B1 | | 3/2002 | Mirkin et al. | |
| 6,645,776 B2 | * | 11/2003 | Kulmala et al. | ............ 436/518 |
| 6,699,501 B1 | * | 3/2004 | Neu et al. | .................. 424/463 |
| 6,720,072 B1 | * | 4/2004 | Hinterwaldner et al. | .... 428/403 |
| 2004/0014073 A1 | * | 1/2004 | Trau et al. | ..................... 435/6 |
| 2005/0123765 A1 | * | 6/2005 | Ong et al. | ............... 428/411.1 |

OTHER PUBLICATIONS

J. S. Arney, "*Oxidation Kinetics and Reciprocity Behavior in the Microencapsulated Acrylate Imaging Process*", Journal of Imaging Science, vol. 31, No. 1, pp. 27-30 (Jan./Feb. 1987).

J. S. Arney and J. A. Dowler, "*Dye Control Mechanisms in the Microencapsulated Acrylate Imaging Process*", Journal of Imaging Science, vol. 32, No. 3, pp. 125-128 (May/Jun. 1988).

E. Mathiowitz et al., "*Photochemical Rupture of Microcapsules: A Model System*", Journal of Applied Polymer Science, vol. 26, No. 3, pp. 809-822 (Mar. 1981).

* cited by examiner

*Primary Examiner*—Ann Y. Lam

(57) ABSTRACT

The present invention relates to the detection of analyte(s) of interest in a test sample using a rupturable microcapsule biosensor. In general, the microcapsule biosensor includes a microcapsule comprising a shell encapsulating a detectable agent and further includes a probe that is joined to the shell of the microcapsule. The present invention contemplates generally using the microcapsule biosensor to determine if a test sample contains an analyte of interest by exposing the microcapsule biosensor to the test sample and allowing the probe to potentially bind to the analyte. External force is applied to the microcapsule to rupture the shell releasing the detectable agent and thereby indicating the presence of the analyte of interest in the test sample.

18 Claims, No Drawings

MICROCAPSULE BIOSENSORS AND METHODS OF USING THE SAME

FIELD OF INVENTION

The present invention relates to microcapsule biosensors and methods of using the same for the detection of analytes.

BACKGROUND OF INVENTION

Life sciences research including biological, biomedical, genetic, agriculture, chemical, and environmental research demands the ability to detect, identify, and often quantify biological agents. Conventional methods of detecting biological agents include using fluorescent dyes to label such agents. Fluorescent labeling normally involves the use of an organic dye molecule bound to a moiety, which, in turn, selectively binds to a particular biological agent, the presence of which is then identified by excitation of the dye molecule to cause the dye molecule to fluoresce. Radioimmunoassays (RIA) have also been used to quantify biological agents using high-specific radioactive isotopes as tracers. RIA normally involves the use of a radioactive isotope bound to a moiety, which, in turn, selectively binds to a particular biological agent. The radioactive isotopes emit small amounts of radiation which are detected by a "gamma camera" thereby indicating the presence of the biological agent. Radioactive isotopes and fluorescent dyes, however are disadvantageous in that handling, storing, and disposing of these tracers are troublesome. Therefore, alternative analytical methods have been employed in place of these techniques.

For example, U.S. Pat. No. 5,128,241 describes a microcapsule with a lipid molecular membrane (e.g. a lyposome) encapsulating a labeling substance and having an antibody attached to the surface thereon. After an antigen is introduced to the microcapsule, a reagent is added that has lytic activity in the presence of an antigen-antibody complex. The microcapsule thereby undergoes lysis by the reagent and releases the labeling substance. This method however, requires the step of adding a reagent to lyse the microcapsule and requires the specific presence of an antibody-antigen complex and a reagent that reacts to the antibody-antigen complex.

Accordingly, there is a need in the art for an indicator that can be readily handled and conveniently stored and that has broad applicability to different analytes.

SUMMARY OF INVENTION

The present invention provides for a microcapsule biosensor for detecting an analyte. The microcapsule biosensor comprises a microcapsule comprising a shell encapsulating a detectable agent, the microcapsule being rupturable under the application of external force. The microcapsule biosensor further comprises a probe joined to the shell of the microcapsule.

The present invention also provides for a kit for detecting an analyte. The kit comprises a rupturable microcapsule biosensor comprising a microcapsule comprising a shell encapsulating a color-forming substance. The rupturable microcapsule biosensor further comprises a probe joined to the shell of the microcapsule. The kit further comprises a developer sheet comprising a substrate coated with a developer layer. The color-forming substance of the microcapsule is capable of reacting with the developer layer of the developer sheet to form a color image on the substrate of the developer sheet. The kit optionally comprises a support immobilized with a capture ligand that is capable of binding the analyte.

The present invention moreover provides a method of detecting an analyte. The method comprises providing a microcapsule biosensor comprising a microcapsule comprising a shell encapsulating a detectable agent, wherein the microcapsule is rupturable under the application of external force. The microcapsule biosensor further comprises a probe joined to the shell of the microcapsule. The method further comprises exposing an analyte to the microcapsule biosensor and allowing the probe to bind to the analyte. The method moreover comprises applying external force to the microcapsule to rupture the shell to release the detectable agent and then detecting the detectable agent. In one embodiment, the method further comprises exposing the released detectable agent to a developer sheet comprising a substrate coated with a developer layer. The method additionally comprises allowing the released detectable agent to react with the developer layer to form an image on the substrate and detecting the image on the substrate.

DETAILED DESCRIPTION OF INVENTION

The present invention relates to the detection of analyte(s) using a rupturable microcapsule biosensor. By "analyte" is meant a substance being assayed either qualitatively, quantitatively, or both. Although the present invention contemplates various embodiments of a microcapsule biosensor, in general, a microcapsule biosensor is a microcapsule with a probe attached to the outer surface thereof. In general, the analyte is a member of a specific binding pair and the probe is the complementary member of the specific binding pair. The microcapsule of the microcapsule biosensor comprises a shell encapsulating a detectable agent and the probe of the microcapsule biosensor is joined to the shell and is capable of binding the analyte. Although the present invention also contemplates various embodiments of methods of using a microcapsule biosensor, in a general embodiment, to detect the presence of an analyte in a test sample, a microcapsule biosensor is exposed to the test sample containing the analyte and the probe is allowed to bind to the analyte in the test sample. External force is applied to the microcapsule to rupture the shell releasing the detectable agent and thereby indicating the presence of the analyte in the test sample.

With respect to particular details of the present invention, the microcapsule of a microcapsule biosensor of the present invention ruptures under the application physical, chemical, biochemical external force or any combination thereof. Such external force may take any form and includes, for example, chemical erosion, crushing, piercing, pressure, freezing, heat, melting, enzyme degradation, explosion, implosion, sound vibration, ultrasound, microwave, or electrical energy in radiant or non-radiant form. Accordingly, the shell of a microcapsule of the present invention is fabricated of any material known in that art that ruptures under the application of external force. The precise material of the shell would be readily recognizable to one of skill in the art based on the intended application of the microcapsule biosensor of the present invention. Preferably, the material is a polymeric material. More preferably, the material is a film-forming material. Non-limiting examples of a film-forming material useful in the present invention include acrylate, methacrylate and acrylic resins such as polymethylmethacrylate, polyacrylic acid, and polyacrylamide; alkyd resins, such as those produced from esters of ethylene glycol and terephthalic acid; animal glues; cassein; cellulose derivatives, such as hydroethyl cellulose, carboxymethyl cellulose, methyl cellulose, hydroxypropyl cellulose, cellulose acetate, cellulose acetate butyrate, and nitrocellulose; coumarone-indene resin; furam resins, such as those of furfuraldehyde and acetophenome; petroleum hydrocarbon polymer resins, such as the "Piccopale" resins; isobutylene resins, such as polyisobutylene; isocyanate resins, such as isocyanate-polyol, polymers of polyesters and tolylene diisocyanate; melamine resins, such as melamine-formaldehyde; phenolic resins, such as phenol-formaldehyde resins; polyamide resins, such as alkoxy substituted nylon; rubbers, both natural and synthetic, GM-S; shellec; styrene resins such as polystyrene, styrene-divinyl-benzene and styrene-divinyl sulfide; terpene resins, such as polyterpene; urea resins, such as urea-formaldehyde resins, urea acetaldehyde resins, urea-melamine formaldehyde, urea-resorcinol, and polyureas; polyurethanes; vinyl resins, such as polyvinyl chloride, polyvinyl acetate and polyvinyl alcohol; vinylidine resins, such as vinylidine chloride-vinyl chloride; natural and synthetic waxes, such as paraffin and candelilla wax, and zein; ethylene copolymers and terpolymers; polysulfones; polycarbonates; polyphenylene oxide; gelatin including gum arabic; and resorcinol-formaldehyde.

The above-mentioned film-forming materials may be used alone or in combination where compatible. The film-forming materials may also be modified with plasticizers and other modifying agents to provide a desired degree of hardness or to impart certain desired characteristics such as solvent impermeability or water impermeability to the film-forming material. As an example of the latter type of material, formaldehyde may be employed to harden the shell of a microcapsule produced from a water-soluble film-forming material. Non-limiting examples of plasticizers that may be used in the present invention include adipic acid esters, such as dioctyl adipate and dibutyl adipate; biphenyl derivatives, such as chlorinated biphenyl; glycol derivatives, such as polyethylene glycols of molecular weight of 200 to 20,000, phythalyl ethyl glycolate; hydrocarbons, such as the polyaromatic hydrocarbon oils; acid esters and ethers, such as butyl or isoetyl esters and glycol ethers of lauric, oleic, citric, abietic, adipic, azelaic, benzoic, palmitic, phosphoric acids, etc; phthalic acid derivatives, such as dimethyl-, diethyl-, dibutyl-, phthalates; polyesters; sulphonic acid derivatives, such as n-ethyl, o-, p-toluene-sulphonamides; tall oil derivatives, such as the methyl esters of tall oil, etc.

The shell of the microcapsule of a microcapsule biosensor according to the present invention encapsulates a detectable agent. With respect to this detectable agent, the detectable agent may be any agent capable of labeling an analyte of interest. A wide variety of detectable agents suitable for labeling analytes are known to those skilled in the art and are generally applicable to the present invention for the labeling of analytes. The detectable agent may be any substance having a detectable physical, chemical, electrical, or other measurable property. Such detectable agents have been well-developed in the field of gel electrophoresis, column chromatography, solid substrates, spectroscopic techniques, and the like, and in-general, detectable agents useful in such methods may be applied to the present invention. Thus, a detectable agent according to the present invention may be any substance detectable by spectroscopic, photochemical, biochemical, immunochemical, electrical, optical, thermal, chemical, or electrochemical means. In particular, detection of such a detectable agent may be accomplished by any of a variety of known methods, including spectrophotometric or optical tracking of radioactive or fluorescent markers, mass spectroscopy, Raman spectroscopy, UV/VIS spectroscopy, NIR spectroscopy, infrared detection, or other methods which track a molecule based upon size, charge, affinity, pH, or electrochemical signal.

A partial, non-exclusive listing of possible detectable agents according to the present invention include visible dyes, fluorescent moieties, radiolabels, enzymes, substrates, cofactors, inhibitors, chemiluminescent or photoluminescent moieties, magnetic particles, organic compounds, semiconductor nanocrystals, highly scattering particles, chelating agents, and photoinducible charge-separation moieties. More particularly, detectable agents according to the present invention may include fluorescing dyes such as cyanine dyes (see U.S. Pat. No. 6,268,222 incorporated herein by reference), fluorogens such as fluorescein and rhodamine, or fluorescently stained microspheres; radiolabels such as $^{32}P$, $^{14}C$, $^{35}S$ or $I^{125}$; sugars including glucose and sucrose; ionic compounds such as tetrapentylammonium; enzymes such as glucose oxidase, peroxidase, alkaline phosphatase, LacZ, chloamphenicola acetyltransferase(CAT), and horse radish peroxidase; coenzymes such as NAD; radical compounds such as methylviologen; chelating agents such as 5-bromo-2-pyridylazo-5-N-sulfopropylaminoaniline; visible dyes such as Sudan Blue and Rhodamine Blue; luminescent substances such as luminol, bis(2,4,6-trichlorophenyl) oxalate, and N-methylacridium ester; highly scattering particles such as titanium dioxide; colorimetric labels such as colloidal gold or colored glass or plastic (e.g. polystyrene, polypropylene, latex, etc.) beads; nucleic acid intercalators such as ethidium bromide, acridine, and propidium; and organic compounds capable of reacting with heavy metal salts to give colored metal complexes, chelates, or salts.

In a preferred embodiment, the detectable agent is a color-forming substance, such as a chromogenic substance, that is a colorless electron-donating dye precursor compound that reacts with a developer material to generate a dye. Non-limiting examples of such a dye precursor chromogenic substance include substantially colorless compounds having in their partial skeleton a lactone, a lactam, a sultone, a spiropyran, an ester or an amino structure. Specifically, the chromogenic substance may be a triarylmethane compound, bisphenylmethane compound, xanthene compound, thiazine compound, or spiropyran compound. Non-limiting examples of such compounds include Crystal Violet lactone, benzoyl leuco methylene blue, Malachite Green Lactone, p-nitrobenzoyl leuco methylene blue, 3-dialkylamino-7-dialkylamino-fluoran, 3-methyl-2,2'-spirobi(benzo-f-chrome), 3,3-bis(p-dimethylaminophenyl) phthalide, 3-(p-dimethylaminophenyl)-3-(1,2dimethylindole-3-yl)phthalide, 3-(p-dimethylaminophenyl)-3-(2-methylindole-3-yl)phthalide,3-(p-dimethylam inophenyl)-3-(2-phenylindole-3-yl)phthalide, 3,3-bis(1,2-dimethylindole-3-yl)-5-dimethylaminophthalide, 3,3-bis-(1,2-dimethylindole-3-yl)6-dimethylaminophthalide, 3,3-bis-(9-ethylcarbazole-3-yl)-5-dimethylaminophthalide, 3,3-bix(2-phenylindole-3-yl)-5-dimethylaminophthalide, 3-p-dimethylaminophenyl-3-(1-methyl pyrrole-2-yl)-6-dimethylaminophthalide, 4,4'-bis-dimethylaminobenzhydrin benzyl ether, N-halophenyl leuco Auramine, N-2,4,5-trichlorophenyl leuco Auramine, Rhodamine-B-anilinolactam, Thodamine-(p-nitroanilino) lactam, Rhodamine-B-(p-chloroanilino)lactam, 3-dimethylamino-6-methoxyfluoran, 3-diethylamino-7-methoxyfluoran, 3-diethylamino-7-chloro-6-methylfluoroan, 3-diethylamino-6-methyl-7-anilinofluoran, 3-diethylamino-7-(acetylmethylamino)fluoran, 3-diethylamino-7-(dibenzylamino)fluoran, 3-diethylamino-7-(methylbenzylamino) fluoran, 3-diethylamino-7-(chloroethylmethylamino)

fluoran, 3-diethylamino-7-(diethylamino)fluoran, 3-methyl-spiro-dinaphthopyran, 3,3'-dichloro-spiro-dinaphthopyran, 3-benzyl-spiro-dinaphthopyran, 3-methyl-naphtho-(3-methoxybenzo)-spiropyran, 3-propyl-spirodibenzoidipyran, etc. Mixtures of these dye precursor chromogenic substances may also be used if desired.

In another embodiment of the present invention, the microcapsule of a microcapsule biosensor according to the present invention contains a color-forming substance, such as a chromogenic material, and additionally contains a photosensitive composition. The photosensitive composition includes a photopolymerizable substance that undergoes a change in viscosity upon exposure to light (such as a radiation curable material). Alternatively, the photosensitive composition includes a photoinitiator and a photopolymerizable substance that undergoes a change in viscosity upon exposure to light in the presence of a photo initiator.

In yet another embodiment, the microcapsule encapsulates a photoacid in addition to a detectable agent. The photoacid may be used to hydrolyse the shell of the microcapsule when the microcapsule is desired to be ruptured.

A microcapsule biosensor of the present invention includes a probe that is joined, either directly or indirectly, to the shell of the microcapsule and that is capable of binding to the analyte of interest. The shell may be modified to be covalently or non-covalently joined to the probe. In the most general embodiment of a probe, the probe is a member of a specific binding pair and the analyte is the complementary member of the specific binding pair. In other words, the microcapsule is derivitized with a specific binding pair member in order to detect the presence of the complementary specific binding pair member (the analyte) in a test sample.

A probe that is a specific binding pair member according to this embodiment of the present invention, may be a ligand or a receptor. As used herein, the term ligand means any organic compound for which a receptor naturally exists or can be prepared. As used herein, a receptor is any compound or composition capable of recognizing a spatial or polar organization of a molecule such as, for example, an epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; polysaccharides; and carbohydrates. Representative specific binding pairs are shown in Table 1.

TABLE 1

Representative Specific Binding Pairs

| | |
|---|---|
| Antibody | Antigen |
| Hapten | Antihapten |
| Biotin | Avidin (or Streptavidin) |
| IgG | Protein A or Protein G |
| Drug Receptor | Drug |
| Toxin Receptor | Toxin |
| Carbohydrate | Lectin |
| Peptide Receptor | Peptide |
| Protein Receptor | Protein |
| Carbohydrate Receptor | Carbohydrate |
| Polynucleotide Binding Protein | Polynucleotide |
| DNA (RNA) | aDNA (aRNA) |
| Enzyme | Substrate |

In an embodiment of a probe of a microcapsule biosensor according to the present invention, the probe is indirectly joined to the shell. In particular, a linking agent is positioned between the shell and the probe and joins the probe to the shell of the microcapsule biosensor through covalent coupling, for example. In one embodiment, the linking agent is a functional group such as, for example, a carboxylate, ester, alcohol, carbamide, aldehyde, amine, sulfur oxide, nitrogen oxide, or halide group. Further examples of suitable functional groups include alkylamino-, arylamino-, isocyano-, cyano-, isothiocyano-, thiocyano-, carboxy-, hydroxy-, mercapto-, phenol-, imidiazole-, aldehyde-, epoxy-, thionyl halide-, sulfonyl halide-, nitrobenzoyl halide-, carbonyl halide-, triazo-, succinimido-, anydride-, haloacetate-, hydrazino- and dihalo triazinyl groups. In a preferred embodiment, the functional group is a carboxylate group.

In another embodiment, the linking agent is a cross-linking agent. For example, if a probe to be joined to the shell is an antigen, the antigen may be attached to the shell through a cross-linking agent such as SPDP (N-succinimidyl-3-(2-pyridylthio)propionate, SMPB (N-succinimidyl-4 (p-maleimideophenyl)butyrate) or the like.

With respect to the size of a microcapsule biosensor of the present invention, as will be appreciated by those skilled in the art, the microcapsule's sensivitity to rupturing under application of external force is dependent upon the overall diameter of the microcapsule as well as the thickness of the shell. Generally, microcapsules of the present invention with greater diameters have greater tendency to rupture than microcapsule with smaller diameters. Similarly, microcapsules with thinner shells have greater tendency to rupture than microcapsules with thicker shells. As such, the diameter of a microcapsule of a microcapsule biosensor of the present invention and the thickness of the shell should be selected such that the microcapsule is neither difficult to rupture nor prone to rupture prematurely. Preferably, the diameter of a microcapsule ranges from about 1 micron to about 25 microns. More preferably, the diameter of a microcapsule ranges from about 5 microns to about 10 microns. With respect to the shell thickness in relation to the diameter of a microcapsule, the shell thickness is preferably about $\frac{1}{10}$ to about $\frac{1}{3}$ of the diameter of the microcapsule.

A microcapsule of a microcapsule biosensor of the present invention may be produced by a number of procedures known in the art. For example, a microcapsule may be made by chemical processes such as phase separation from both aqueous and organic solvent solutions; solvent exchange in preformed microcapsules; interfacial polymerization; and melt techniques, which are described in U.S. Pat. No. 3,469,439, which is incorporated herein by reference. A microcapsule may also be fabricated by polymerization of one or more monomers in oil; coacervation; and various dispersing and cooling methods. For example, an oil solution of the detectable agent (the internal phase) may be dispersed in a continuous phase containing the film-forming material, and the resulting emulsion may be microencapsulated by, for example, coacervation or interfacial polymerization. Open phase systems can be prepared by dispersing the internal phase in a solution of a polymeric binder and adjusting the viscosity of the dispersion for coating. Suitable binders include, for example, gelatin, polyvinyl alcohol, polyacrylamide, and acrylic lattices. A microcapsule may also be made by mechanical processes such as vacuum metallizing, fluidized bed coating, and centrifugal casting. Material and approaches for manufacturing microcapsules are described in U.S. Pat. No. 623,522 and U.S. Pat. No. 365,187, both of which are hereby incorporated by reference.

A microcapsule biosensor of the present invention may be used in a wide variety of assays known in the art. In particular, the microcapsule biosensor of the present invention may be used in assays that utilize specific binding pair members to detect the presence of an analyte of interest in a test sample. Such assays and techniques include, for example, immunoassays, enzyme-based assays, nucleic acid probe assays, hybridization or immunoblotting techniques, DNA sequencing, flow cytometry, fluorescence imaging, and microscopy. In general, these assays include a detectable agent that becomes associated with the complex formed by binding of the analyte of interest to its specific bind pair member and thereby facilitates detection of the complex. Detection of the complex is an indication of the presence and possible quantity of the analyte, depending on the assay format. The analyte may be any substance desired to be detected in a test sample and includes for example, pharmaceutically active agents, proteins, peptides, polypeptides, polynucleotides, DNA, and RNA. Test samples include biological samples such as whole blood, serum, urine, saliva and tissue samples, soil samples, water samples and food samples.

Although the present invention contemplates the use of a microcapsule biosensor for a wide variety of applications, a microcapsule biosensor of the present invention is particularly useful for high-throughput screening of a plurality of analytes as a microcapsule biosensor allows for spatial and, in certain instances, spectral multiplexing. As discussed in more detail below, in spatial multiplexing, a plurality of capture ligands that are each capable of binding a specific analyte of the plurality of analytes are immobilized on a support in a spatially-arrayed pattern. The identity of a capture ligand at each coordinate is known, so that when a test sample is introduced to the array of capture ligands, and microcapule biosensors are subsequently exposed to the array, the identity of the analytes can be deduced. In spectral multiplexing, a plurality of microcapsule biosensors that each encapsulate a detectable agent that emits a distinct color signal associated with a specific analyte are utilized. The identify of an analyte is determined by the color of the signal emitted by the detectable agent of the microcapsule biosensor bound to the analyte.

One exemplary use of a microcapsule biosensor according to the present invention involves a competition type assay where "capture ligands" that specifically bind to the analytes of interest are immobilized on a support. For purposes of illustration, the present embodiment and other embodiments described herein are described in terms of a plurality of capture ligands, a plurality of microcapsule biosensors, and a plurality of analytes (such analytes either being the same or being different from one another depending on the particular assay). It is also contemplated by the present invention, that a single capture ligand and a single microcapsule biosensor be utilized to detect a single analyte. Further, in this embodiment and all other embodiments of the present invention where capture ligands are immobilized on a support, the support may be fabricated of any sufficiently rigid material that can withstand the application of external force thereon, upon which biological moieties can be immobilized, and upon which an image formed by release of the detectable agent can be created. For example, the support may comprise glass, plastic or other polymer. The support may also be coated to "fix" the released detectable agent on the support. For example, the support may be optically designed to create an interference pattern to reveal or enhance the presence of a thin "film" layer created by the rupturing of the microcapsules. For instance, a silicon support preferably coated with a thin (about 500 nanometers) oxide layer (such as, for example, silicon dioxide) may be suitable to reveal the presence of a thin film of a polymeric resin that may be hardened by the fixing process under the proper illumination. The thin film layer, essentially, may serve as the surface that absorbs the image created by the released detectable agent.

In a competition-type assay, once the support is immobilized with capture ligands, a known quantity of tagged reference molecules (such molecules having the same identity as the analytes of interest) and a test sample potentially containing an unknown quantity of untagged analytes of interest are utilized. By "tagged" it is meant that each reference molecule is bound to a probe of a microcapsule biosensor according to the present invention. The microcapsule biosensors may contain any type of detectable agent, such as, for example, a fluorescent dye. In this type of assay, the fluorescence emission from the tagged reference molecules is measured in the absence of the test sample to provide a reference fluorescence emission measurement. The known quantity of tagged reference molecules is then mixed with the test sample potentially containing the unknown quantity of the analytes of interest and the resulting mixture is exposed to the support. Sufficient external force is applied to the support to rupture the microcapsule of the microcapsule biosensor and expose the fluorescent dyes contained in the microcapsule. The fluorescence emitting from the support after exposure to the test sample is compared to the reference fluorescence emission measurement. A fluorescence emission weaker than the reference fluorescence emission measurement indicates the binding of the analytes of interest to the capture ligands and therefore indicates the presence and quantity of the analytes of interest in the test sample.

Another exemplary use of the microcapsule biosensor according to the present invention involves a sandwich-type of assay, where captor ligands that specifically bind to the analytes of interest are immobilized on a support. A test sample potentially containing the analytes of interest is exposed to the support to allow the analytes to bind to the capture ligands. The support may be subsequently washed to remove any unbound analytes. Further according to this embodiment of the present invention, microcapsule biosensors are exposed to the support. The microcapsules of the microcapsule biosensors may contain, for example, a fluorescent dye as the detectable agent. The probes of the microcapsule biosensors are allowed to potentially bind to the analytes bound to the capture ligands. The support may be subsequently washed to remove any unbound microcapsule biosensors. Sufficient external force is then applied to the support to rupture the microcapsule and to expose the fluorescent dyes contained therein. Fluorescent emission (if any) from the exposed fluorescent dyes is detected to determine if the analytes of interest are present in the test sample. The quantity of the analytes can also be determined based on the intensity of the fluorescent emission.

In another embodiment of a sandwich-type assay, microcapsule biosensors according to the present invention are immobilized on a support. The microcapsule biosensors may be immobilized on the support via any method known in the art. For example, in one embodiment, Self-Assembled Monolayers (SAMs) are immobilized on the support and functionalized with biotin molecules, for example. Methods of forming SAMs on a support, suitable materials for the support, and methods of functionalizing SAMs with different functional groups for an intended purpose are well-known to one of skill in the art. Further according to this embodiment, microcapsule biosensors are functionalized with ligands, such as avidin molecules, for example, which bind to the biotin molecules of the SAMs and therefore immobilize the microcapsule biosensors to the support. Each of the microcapsules of the microcapsule biosensors may contain, for example, a fluorescent dye as the detectable agent. A test sample potentially containing the analytes of interest is exposed to the support and the analytes are allowed to potentially bind to the probes of the microcapsule biosensors. Sufficient external force is applied to the support to rupture the microcapsules and expose the fluorescent dyes contained therein. Fluorescent emission (if any) from the exposed fluorescent dyes is detected to determine if the analytes of interest are present in the test sample. The quantity of the analytes can also be determined based on the intensity of the fluorescent emission.

In one particular embodiment of a method of using a microcapsule biosensor of the present invention, the detectable agent of the microcapsules is a color-forming substance and upon rupturing of the microcapsule, the color-forming substance is exposed to a developer sheet, which is a substrate coated with a developer layer. The developer layer is a layer of developer material. The color-forming substance reacts with the developer material of the developer layer and forms a color image on the substrate. In the context of the present invention, the color-forming substance may produce an image of any color perceived by the human eye, including the color black. Preferably the microcapsules described in U.S. Pat. Nos. 5,916,727, 6,080,520, and 6,127,084, all assigned to Cycolor Incorporated (which are incorporated by reference herein) are used in this embodiment.

With respect to particular details of this embodiment according to the present invention, capture ligands that are capable of binding to the analytes of interest are immobilized on a substrate. For example, where the analytes of interest are a particular nucleotide sequence, the capture ligands would be the complementary nucleotide sequences. A test sample potentially containing the analytes of interest is exposed to the support to allow for potential binding of the analytes to the capture ligands. The support may be washed to remove any unbound analytes. Microcapsule biosensors are then introduced to the support to bind to the analytes of interest and the support may be subsequently washed to remove any unbound microcapsule biosensors. The support is then contacted with the developer sheet wherein the microcapsule biosensors bound to the analytes of interest are contacted with the developer layer of the developer sheet. External force is applied to the support and/or the developer sheet to rupture the microcapsules and release the color-forming substances to the developer sheet. Upon transfer of the color-forming substances to the developer sheet, the color-forming substances react with the developer layer and form color images on the substrate. The precise location of the analytes (if present) can be determined based on the location of the color images on the substrate. The quantity of the analytes can also be determined based on the intensity of the fluorescent emission. Although the preceding description describes the application of a microcapsule biosensor in a sandwich assay, this embodiment of a microcapule biosensor may also be utilized in a competition assay employing the same mechanisms and procedures.

In an alternative embodiment, in addition to containing a color-forming substance, the microcapsules also contain photosensitive compositions. As previously mentioned, the photosensitive composition may include a 1) photoinitiator and a polymerizable substance that undergoes a change in viscosity upon exposure to light in the presence of the photoinitiator or 2) simply a polymerizable substance that undergoes a change in viscosity upon exposure to light.

In this embodiment according to the present invention, capture ligands that are capable of binding to the analytes of interest are immobilized on a substrate. A test sample potentially containing the analytes of interest is exposed to the support to allow for potential binding of the analytes to the capture ligands. The support may be washed to remove any unbound analytes. Microcapsule biosensors, each microcapsule containing a color-forming substance and photosensitive composition, are then introduced to the support to bind to the analytes of interest. The support may be subsequently washed to remove any unbound microcapsule biosensors. The support is then contacted with a developer wherein the microcapsule biosensors bound to the analytes of interest are contacted with the developer layer of the developer sheet. External force is applied to the support and/or the developer sheet to rupture the microcapsules and release the color-forming substances and photosensitive compositions to the developer sheet. Upon transfer of the color-forming substances to the developer sheet, the color-forming substances react with the developer layer and form color images on the substrate. The substrate is irradiated causing the photoinitiator and the polymerizable substance to co-polymerize thereby gelling, solidifying or otherwise immobilizing the color-forming substance. Immobilization of the color-forming substance is particularly advantageous as this prevents an image formed by a color-forming substance to "bleed" into an adjacent image formed by a color-forming substance.

The present invention also contemplates other mechanisms by which the color-forming substance or other detectable agent is immobilized such as by using heat (thermosetting), air (oxidation or solvent evaporation), chemically induced precipitation or phase separation (non-solvent "wash").

The color-forming substance contained in the microcapsule of the microcapsule biosensor according to the above-described embodiment, may be any color-forming substance that can be encapsulated and that will react with a developer material to form a color image. For example, the color-forming substance may be an organic chemical that is capable of reacting with heavy metal salts to give colored metal complexes, chelates, or salts. The color-forming substance may also be a chromogenic substance. Representative examples of chromogenic substances have already been disclosed above and apply to this embodiment. In general, the color-forming substance for use in this embodiment according to the present invention, may be an electron-donating type compound. In a preferred embodiment, the color-forming substance is silver acetate.

In embodiments where the microcapsule also contains a polymerizable substance, the polymerizable substance may be a monomer, dimer, or oligomer which is polymerized to a higher molecular weight compound or may be a polymer that is cross-linked. Preferably the polymerizable substance is a radiation curable material that preferably is curable by free radical initiated chain propagated addition polymerization or ionic polymerization. Substantially any photopolymerizable substance that can be encapsulated and that does not interfere with the image-forming capability of the color-forming substance may be used. These substances may be inherently sensitive to actinic radiation, in which case they may be hardened without a photoinitiator. In a more preferred embodiment, the radiation curable material is an ethylenically unsaturated organic compound.

In circumstances where a photoinitiator according to the present invention is utilized, the photoinitiator may be a compound that absorbs the exposure radiation and generates a free radical alone or in conjunction with a sensitizer. Conventionally, there are homolytic photoinitiators which cleave to form two radicals and initiators which radiation converts to an active species which generates a radical by abstracting a hydrogen from a hydrogen donor. There are also initiators which complex with a sensitizer to produce a free radical generating species and initiators which otherwise generate radicals in the presence of a sensitizer. Both types can be used in the present invention. If ionic polymerization is used to tie up the color-forming substance, the initiator may be the anion or cation generating type depending on the nature of the polymerization. Where ultraviolet light is exposed to the substrate, suitable photoinitiators include α-alkoxy phenyl ketones, O-acylated α-oximinoketones, polycylic quinones, benzophenones and substituted benzophenones, xanthones, thioxanthones, halogenated compounds such as chlorosulfonyl and chloromethyl polynuclear aromatic compounds, chlorosulfonyl and chloromethyl heterocyclic compounds, chlorosulfonyl and chloromethyl benzophenones and fluorenones, haloalkanes, α-halo α-phenylacetophenones; photoreducible dye-reducing agent redox couples, halogenated paraffins (e.g., brominated or chlorinated paraffin) and benzoin alkyl ethers.

The developer material of the developer layer of this embodiment is made of any material capable of reacting with the color-forming substance to produce a color image on the substrate. In the most typical case, the developer material is an electron-accepting compound. In the broadest sense, however, the term "developer material" as used herein refers to that half of the color-forming reactant combination that is not encapsulated in the microcapsule. Hence, compounds conventionally recognized as color developers may be encapsulated as the color-forming substance in a microcapsule and compounds conventionally recognized as color-formers may be used outside a microcapsule according to the present invention. The developer materials used in the present invention are those conventionally employed in carbonless paper technology and are well known. Illustrative specific examples are clay minerals such as acid clay, active clay, attapulgite; organic acids such as tannic acid, gallic acid, propyl gallate; acid polymers such as phenol-formaldehyde resins, phenol acetylene condensation resins, condensates between an organic carboxylic acid having at least one hydroxy group and formaldehyde; metal salts or aromatic carboxylic acids such as zinc salicylate, tin salicylate, zinc 2-hydroxy naphthoate, zinc 3,5 di-tert butyl salicylate, oil soluble metal salts of phenol-formaldehyde novalak resins such as zinc modified oil soluble phenol-formaldehyde resins, zinc carbonate and mixtures thereof. In a preferred embodiment, the developer material is titanium oxide or titanium dioxide. When used in a developer sheet, the developer material may be mixed with a binder such as latex, polyvinyl alcohol, maleic anhydride-styrene copolymer, starch and gum arabic. It understood by one of skill in the art that all binders well-known as film-forming materials may be used in this capacity.

The developer sheet of this embodiment of the present invention also includes a substrate. In the context of this embodiment of the present invention, the substrate may be any material that is capable of retaining a color image created by the reaction of the color-forming substance and the developer material of the developer layer. For example, the substrate may be manufactured of a material to provide for an adsorbing or absorbing surface. For example, the substrate may be white enamel paper, glass, plastic, or other polymeric material. In embodiments where a glass substrate, for example, is utilized, the microcapsule may contain a polymeric material in addition to the color-forming substance to facilitate the retention of a color image on the substrate. Alternatively, the substrate may be treated with a coating, such as a silicon gel, to facilitate retention of a color image on the substrate.

As mentioned previously, a microcapsule biosensor of the present invention allows for spatial and, in certain instances, spectral multiplexing. With respect to spatial multiplexing, by employing a plurality of microcapsule biosensors that each release a detectable agent at a precise location on a support or substrate upon rupture, the microcapsule biosensors provide for spatial multiplexing as the identification of the analyte may be determined by the location of the signal released by the detectable agent. For example, in the context of the aforementioned embodiment wherein the detectable agent is a color-forming substance and a developer sheet is utilized, if it is desired to screen a test sample for a variety of different analytes, each microcapsule biosensor may contain a color-forming substance and the presence of the analyte of interest may be determined by the location of the color image on the substrate.

With respect to particular details of an exemplary use of this particular embodiment, if it is desired to screen a test sample for a plurality of different analytes, a plurality of capture ligands that are each capable of binding a specific analyte of the plurality of different analytes are immobilized on a support in a spatially-defined pattern. Such spatially-defined pattern of the capture ligands allows the presence of a specific analyte to be determined based on the location of the capture ligand to which it binds. A test sample is introduced to the support to allow for potential binding of analytes to their respective capture ligands. A plurality of microcapsule biosensors are then exposed to the support with each microcapsule biosensor including a probe capable of binding to a specific analyte of the plurality of different analytes and each microcapsule containing a color-forming substance encapsulated therein. The support is then contacted with a developer sheet wherein the microcapsule biosensors bound to the analytes of interest are placed in contact with the developer layer of the developer sheet. External force is applied to the support and/or the developer sheet to rupture the microcapsules and transfer the color-forming substance of each microcapsule to the developer sheet. Upon transfer of each color-forming substance to the developer sheet, each color-forming substance reacts with the developer layer and forms a color image on the substrate. The presence and identity of the analyte(s) is determined based on the location of the color image(s) formed on the substrate. The quantity of the analyte(s) can also be determined based on the intensity of the fluorescent emission.

Several methods are known in the art to immobilize capture ligands on a support in a spatially defined pattern. For example in one embodiment, capture ligands are patterned on the support by photolithography using a photoreactive group on a coupling agent. Such a technique is disclosed in McGall et al. U.S. Pat. No. 5,412,087, which is incorporated in its entirety herein. In this embodiment, thiopropionate having a photochemically removable protecting group is covalently coupled to functional groups on the surface of the support. Light of the appropriate wavelength is then used to illuminate predefined regions of the surface according to a predetermined pattern, resulting in photo deprotection of the thiol group. A mask may be used to ensure that photo deprotection only takes place at the desired sites according to the desired pattern. Capture ligands containing thiol reactive groups, such as maleimides, are then exposed to the support and react with the deprotected regions. The unbound capture ligands are then washed away, and the patterning process may be repeated at another location with another capture ligand that binds another analyte of interest. Capture ligands may also be patterned on the support through the use of SAMs as discussed above.

The present invention also contemplates spectral multiplexing by employing a plurality of microcapsule biosensors that each encapsulate a detectable agent that emits, produces, or releases a distinct color signal associated with a specific analyte. The identification of a specific analyte is determined by the color of the signal emitted, produced or released by the detectable agent. In the context of the aforementioned embodiment wherein the detectable agent is a color-forming substance and a developer sheet is utilized, the microcapsule of each microcapsule biosensor encapsulates a color-forming substance that forms a specific color that is associated with a specific analyte when the color-forming substance reacts with the developer layer on the developer sheet.

With respect to particular details of an exemplary use of this particular embodiment, if it is desired to screen a test sample for a plurality of different analytes, for example, a support immobilized with capture ligands that are each capable of binding a specific analyte of the plurality of different analytes is provided. The test sample is introduced to the support allowing for binding of analytes to their respective capture ligands. A plurality of microcapsule biosensors are then exposed to the support with each microcapsule biosensor including a probe being capable of binding to a specific analyte of the plurality of different analytes and the microcapsule of each microcapsule biosensor containing an analyte-specific color-forming substance encapsulated therein. By "analyte-specific color-forming substance" is meant that each color-forming substance encapsulated in each microcapsule forms a specific color that is associated with a specific analyte when the color-forming substance is exposed to the developer material of the developer layer. The support is then contacted with a developer sheet wherein the microcapsule biosensors bound to the analytes of interest are placed in contact with the developer layer of the developer sheet. External force is applied to the support and/or the developer sheet to rupture the microcapsules and transfer the analyte-specific color-forming substances of each microcapsule to the developer sheet. Upon transfer of each analyte-specific color-forming substance to the developer sheet, each analyte-specific color-forming substance reacts with the developer layer and forms a particular color image on the substrate. The presence and identity of the analyte(s) is determined based on the color of the image(s) formed on the substrate. The quantity of the analyte(s) can also be determined based on the intensity of the fluorescent emission.

One illustrative example of a use of this assay is in the area of pathogen detection. If a single blood sample needs to be screened for a plurality of different pathogens, then antibodies that each uniquely bind to a specific pathogen of the plurality of different pathogens are immobilized on a support. For example, if it is desired to screen for the presence of anthrax, small pox, ebola, and malaria in a single blood sample, then the support may be immobilized with an antibody for anthrax, an antibody for small pox, an antibody for ebola, and an antibody for malaria. The test blood sample is then introduced to the support and the pathogen(s) (if present) bind to their respective antibodies on the support. A plurality of microcapsule biosensors are exposed to the support with each microcapsule biosensor including a probe capable of binding to a specific pathogen of the plurality of different pathogens and the microcapsule of each microcapsule biosensor containing a pathogen-specific color-forming substance encapsulated therein. For example, the microcapsule biosensor that includes a probe that is capable of binding to the anthrax pathogen could contain a color-forming substance that forms a green color on the substrate after reacting with the developer layer; the microcapsule biosensor that includes a probe that is capable of binding to the smallpox pathogen could contain a color-forming substance that forms a red color on the substrate after reacting with the developer layer; and so forth. The support is then contacted with a developer sheet wherein the microcapsule biosensors potentially bound to their respective pathogens are placed in contact with the developer layer of the developer sheet. External force is applied to the support and/or the developer sheet to rupture the microcapsules and transfer the pathogen-specific color-forming substance of each microcapsule to the developer sheet. Upon transfer of each pathogen-specific color-forming substance to the developer sheet, each pathogen-specific color-forming substance reacts with the developer layer and forms a particular color image on the substrate. The presence and identity of the pathogen(s) is determined based on the color of the image(s) formed on the substrate. In this particular example, a green color image on the substrate indicates the presence of the anthrax pathogen and a red color image on the substrate indicated the presence of the smallpox pathogen. It is understood, of course, that these particular color images are described for illustrative purposes only, and any color image and therefore any color-forming substance may be associated with any particular pathogen. It is also understood that the color-forming substance is only an example of a detectable agent that provides for spectral multiplexing. Any detectable agents, including for example, visible dyes and fluorescing dyes, that are capable of emitting or releasing a two or more distinct color signals allow for spectral multiplexing.

Throughout this application, reference has been made to various publications, patents, and patent applications. The teachings and disclosures of these publications, patents, and patent applications in their entireties are hereby incorporated by reference into this application to more fully describe the state of the art to which the present invention pertains.

The aforementioned descriptions of uses of the microcapsule biosensors of the present invention are only exemplary and various other applications of the microcapsule biosensors of the present invention, as well as variations in the above-described methods, will be readily appreciated by one of skill in the art. It will also be appreciated that the present disclosure is intended to set forth the exemplifications of the invention, and the exemplifications set forth are not intended to limit the invention to the specific embodiments illustrated. The disclosure is intended to cover, by the appended claims, all such modifications as fall within the spirit and scope of the claims.

I claim:

1. A microcapsule biosensor for detecting an analyte comprising: a microcapsule comprising a shell encapsulating a detectable agent, wherein the microcapsule is rupturable under the application of external force; and the detectable agent is a color-forming substance that reacts with a developer material; a photosensitive composition: and a probe joined to the shell of the microcapsule.

2. The microcapsule biosensor of claim 1, wherein the shell comprises a polymeric material.

3. The microcapsule biosensor of claim 2, wherein the polymeric material comprises a film-forming material.

4. The microcapsule biosensor of claim 1, wherein the microcapsule has a diameter of about 1 micron to about 25 microns.

5. The microcapsule biosensor of claim 1, wherein the shell has a thickness of about 1/10 to about 1/3 the diameter of the microcapsule.

6. The microcapsule biosensor of claim 1, further comprising a ligand linked to the shell and capable of binding, either directly or indirectly, to a support.

7. The microcapsule biosensor of claim 1, wherein the probe is selected from the group consisting of: antibody, antigen, hapten, antihapten, blotin, avidin, streptavidin, lgG, protein A, protein G, drug receptor, drug, toxin receptor, toxin, carbohydrate, lectin, peptide, peptide receptor, protein, protein receptor, carbohydrate receptor, polynucleotide, polynucleotide binding partner, DNA, RNA, enzyme, and enzyme substrate.

8. The microcapsule biosensor of claim 1, further comprising a linking agent that joins the probe to the shell of the microcapsule.

9. The microcapsule biosensor of claim 1, wherein the color-forming substance is a chromogenic substance.

10. The microcapsule biosensor of claim 1, wherein the reaction of the color-forming substance with the developer material results In a dye.

11. A kit for detecting an analyte comprising:
a microcapsule biosensor comprising a rupturable microcapsule comprising a shell encapsulating a color-forming substance, the microcapsule biosensor further comprising a probe that is joined to the shell of the microcapsule; and
a developer sheet comprising a substrate coated with a developer layer.

12. The kit of claim 11, further comprising a support immobilized with a capture ligand.

13. The kit of claim 11, wherein the color-forming substance is a chromogenic substance.

14. The kit of claim 11, wherein the color-fomiing substance reacts with the developer layer.

15. The kit of claim 11, wherein the reaction of the color-forming substance with the developer layer results in a dye.

16. A method of detecting an analyte comprising: providing a microcapsule biosensor comprising a microcapsule comprising a shell encapsulating a detectable agent, wherein the detectable agent is a color-forming substance that reacts with a developer material, and wherein the microcapsule is rupturable under the application of external force, the microcapsule biosensor further comprising a probe joined to the shell of the microcapsule; exposing an analyte to the microcapsule biosensor; allowing the probe to bind to the analyte; applying external force to the microcapsule to rupture the shell and release the detectable agent; and detecting the detectable agent.

17. The method of claim 16, wherein the step of detecting the detectable agent further comprises: exposing the released detectable agent to a developer sheet comprising a substrate coated with a developer layer; allowing the detectable agent to react with the developer layer to form an image on the substrate; and detecting the image on the substrate.

18. The method of claim 17, wherein detecting the image comprises determining the location of the analyte based on the location of the image on the substrate.

* * * * *